(12) United States Patent
Seo et al.

(10) Patent No.: US 11,406,539 B2
(45) Date of Patent: Aug. 9, 2022

(54) FACIAL PROTECTION EQUIPMENT FOR EASY OPERATION OF ROTATING OPENING AND CLOSING

(71) Applicant: SERVORE CO., LTD., Gyeonggi-do (KR)

(72) Inventors: Woon Su Seo, Gyeonggi-do (KR); Jeong Min Seo, Gyeonggi-do (KR)

(73) Assignee: SERVORE CO., LTD., Gyeonggi-do (KR)

(*) Notice: Subject to any disclaimer, the term of this patent is extended or adjusted under 35 U.S.C. 154(b) by 143 days.

(21) Appl. No.: 16/692,451

(22) Filed: Nov. 22, 2019

(65) Prior Publication Data
US 2021/0045921 A1 Feb. 18, 2021

(30) Foreign Application Priority Data

Aug. 13, 2019 (KR) .................. 10-2019-0098943

(51) Int. Cl.
*A61F 9/02* (2006.01)

(52) U.S. Cl.
CPC .............. *A61F 9/025* (2013.01); *A61F 9/022* (2013.01); *A61F 9/027* (2013.01)

(58) Field of Classification Search
CPC .......... A61F 9/025; A61F 9/022; A61F 9/027; A61F 9/02; A61F 9/06; A61F 9/026; A42B 3/085; A42B 3/14; A42B 3/18; A42B 3/185; A42B 3/22; A42B 3/221; A42B 3/222; A42B 3/225
USPC ............................................. 2/426, 428, 8.2
See application file for complete search history.

(56) References Cited

U.S. PATENT DOCUMENTS

| | | | | |
|---|---|---|---|---|
| 4,069,512 A | * | 1/1978 | Palmaer | A42B 3/166 2/209 |
| 9,433,252 B2 | * | 9/2016 | Lebel | A42B 3/326 |
| 2018/0242677 A1 | * | 8/2018 | Pilenga | A61F 9/029 |

FOREIGN PATENT DOCUMENTS

KR 1020140111730 9/2014

* cited by examiner

*Primary Examiner* — F Griffin Hall
(74) *Attorney, Agent, or Firm* — IPLA P.A.

(57) ABSTRACT

A facial protection equipment for an easy operation of rotating opening and closing, includes: a facial protection unit of which one side is supported at one side of a face of an operator and which shields and protects at least the one side of the face of the operator; a fixing unit that is worn on a head of the operator; and a connection member of which one end portion is coupled to one side of the fixing unit to be rotatable in an up-down direction and another end portion is coupled to the facial protection unit, where the connection member has a pivot bracket of which one end portion is coupled to the one side of the fixing unit to be rotatable in the up-down direction.

2 Claims, 9 Drawing Sheets

FACIAL PROTECTION EQUIPMENT FOR EASY OPERATION OF ROTATING OPENING AND CLOSING

CROSS REFERENCE

The present application claims priority to Korean Patent Application No. 10-2019-0098943, filed 13 Aug. 2019, the entire contents of which is incorporated herein by its entirety.

BACKGROUND

The present invention relates to facial protection equipment for an easy operation of rotating opening and closing, more specifically, to facial protection equipment for an easy operation of rotating opening and closing in which a moving bracket of which one side is coupled to a facial protection unit is slidably coupled to one side of a pivot bracket that is rotatably coupled to one side of a fixing unit, and thereby a front-rear moving operation of the facial protection unit for rotating opening and closing can be easily performed.

A welding is a metal processing that joins two or more solid metals into one. A high energy heat source is required for welding and high-pressure and explosive gases such as high voltage electricity, oxygen, acetylene, and argon are used as the energy source. The hazards and dangers caused by the welding are due to a welding fume (metal components contained in the fume), harmful gases, harmful rays, noise, or high temperature environment etc. generated during welding.

The welding fume refers to a small particle formed by the cooling of a material evaporated by heat during welding and is caused by the diffusion of the molten metal vapor around by an arc generation heat of high temperature. In the relationship between the amount of the fume generated in the coated arc welding and the welding current, the greater the current, the voltage, and the electrode diameter, the greater the amount of generation thereof.

In addition, since strong ultraviolet rays and infrared rays, which are harmful rays, have a fatal effect on human eyes, welding masks, welding goggles, and breathing masks with a shading plate are used so as to protect workers from harmful rays and welding fumes during welding.

FIG. 1 is a diagram illustrating a welding car goggles (hereinafter, referred to as a conventional welding car goggles) of the Patent registration No. 1482166 filed by the present applicant in 2012.

As shown in FIG. 1, the welding car goggles includes an automatic shading part (110) that is disposed at a position corresponding to the eyeballs of the worker and shields the eyes of the worker according to the amount of ambient light through LCD lens to protect the eyes of the worker, a fixing band (120) having both end portions connected to both sides of the automatic shading part (110) and is worn on the head of the worker so as to fix the position of the automatic shading part (110), and a skirt (130) that is coupled to the rear end of the fixing band (120) and adhered to the face of the worker.

The conventional welding car goggles (100) detects the light generated during the welding operation and the LCD lens thereof automatically shields the light according to the detected light amount to protect the eyes of the worker from the strong light. Here, as described above, the skirt (130) is adhered to the face of the worker so as to prevent the harmful light, the welding spatter, the grinder scattering dusts, and the fume gas etc. being introduced into the inside thereof.

On the other hand, when the worker does not use welding car goggles (100), which is worn thereon, during the welding operation, the worker raises the automatic shading part (110) above the head to secure more visibility. Here, where the automatic shading part (110) is lifted upwards in a state that the skirt (130) is in close contact with the face of the worker, since the skirt (130) is swept on the face of the worker, the worker pulls the automatic shading part (110) forward and then, lifts it upward.

However, when the fixing band (120) is firmly adhered to the head of the worker to fix the automatic shading part (110), a considerable force is required to pull the automatic shading part (110) forward.

In recent years, the need for a facial protection equipment that can be easily rotated by pulling the automatic shading part (110) forward after the welding operation has been increased.

SUMMARY OF THE INVENTION

The invention is made to solve the problem described above, and an object of the invention is to provide a facial protection equipment for an easy operation of rotating opening and closing in which a moving bracket of which one side is coupled to a facial protection unit is slidably coupled to one side of a pivot bracket that is rotatably coupled to one side of a fixing unit, and thereby a front-rear moving operation of the facial protection unit for rotating opening and closing can be easily performed.

Another object of the invention is to provide a facial protection equipment for an easy operation of rotating opening and closing in which a returning member, which is interposed between a pivot bracket and a connection member, and magnets, which are installed on both the pivot bracket and the connection member at one facing side of each other, enable returning movement of a moving bracket to be automatically performed after the moving bracket is moved, and thereby rotating opening and closing movement of a facial protection unit can be easily performed.

Still another object of the invention is to provide a facial protection equipment for an easy operation of rotating opening and closing in which one side of a free-rotating unit that is coupled to one side of a moving bracket in a freely rotatable manner is supported at one side of an inner surface of a pivot bracket such that at least any one side of the moving bracket is separated from the pivot bracket, and thereby a moving operation of the moving bracket can be more easily performed.

According to an aspect of the invention to achieve the object described above, there is provided a facial protection equipment for an easy operation of rotating opening and closing, including: a facial protection unit of which one side is supported at one side of a face of an operator and which shields and protects at least the one side of the face of the operator; a fixing unit that is worn on a head of the operator; and a connection member of which one end portion is coupled to one side of the fixing unit to be rotatable in an up-down direction and another end portion is coupled to the facial protection unit, wherein the connection member has a pivot bracket of which one end portion is coupled to the one side of the fixing unit to be rotatable in the up-down direction, and a moving bracket of which one end portion is coupled to one side of the pivot bracket to be slidably movable in a length direction of the pivot bracket and another end portion is connected to the one side of the facial protection unit.

Preferably, the connection member further has a returning member that is interposed between the pivot bracket and the moving bracket and supplies an elastic force to the moving bracket in a direction toward the pivot bracket.

Preferably, the connection member has magnets that are attached to both the pivot bracket and the moving bracket at one facing side of each other, and the magnets generate an attractive force to each other.

Preferably, the moving bracket has a moving body that is coupled to the one side of the pivot bracket to be slidably movable in the length direction of the pivot bracket, and a free-rotating member that is coupled to one side of the moving body in a freely rotatable manner and has both end portions which are supported at one side of an inner surface of the pivot bracket.

BRIEF DESCRIPTION OF THE DRAWINGS

The above and other objects, features and advantages of the present invention will be more apparent from the following detailed description taken in conjunction with the accompanying drawings, in which.

REFERENCE SIGNS LIST

Figure 1:
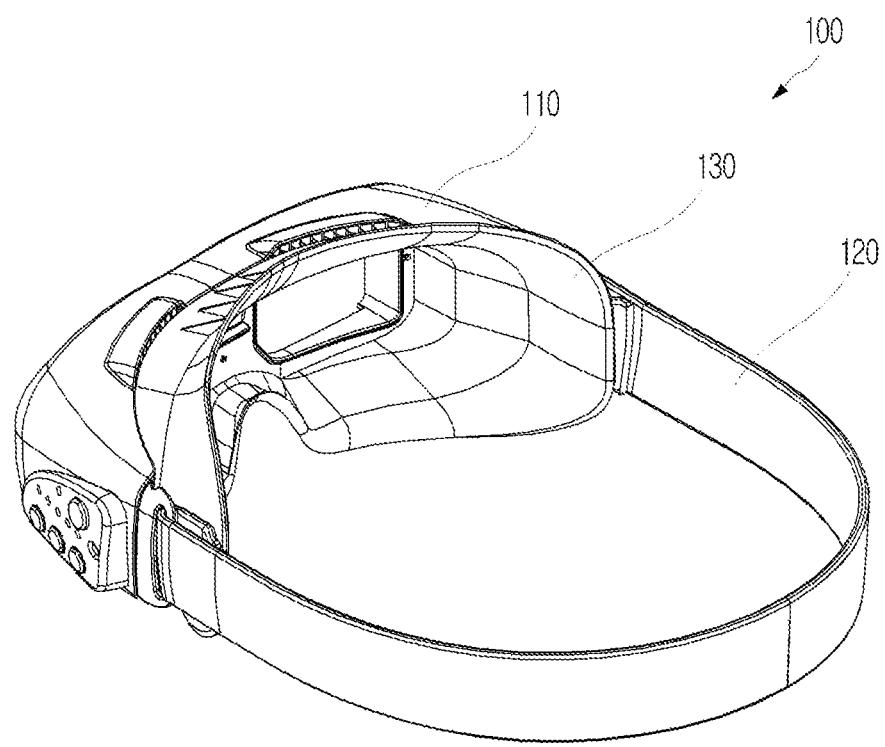
FIG. 1 is a diagram illustrating a welding car goggles (hereinafter, referred to as a conventional welding car goggles) of the Patent registration No. 1482166 filed by the present applicant in 2012.

10: facial protection unit
11: main body
12: light shading lens
13: skirt
20: fixing unit
21: band portion
21a: first band unit
21aa: fixing protrusion
21b: second band unit
22: length adjusting portion
30: connection member
31: pivot bracket
31a: rotation fixing hole
32: moving bracket
32a: moving body
32b: free-rotating member
33: returning member
34: magnets

DETAILED DESCRIPTION OF THE PREFERRED EMBODIMENT

Hereinafter, preferred embodiments of the invention will be described in more detail with reference to the accompanying drawings.

Figure 2:
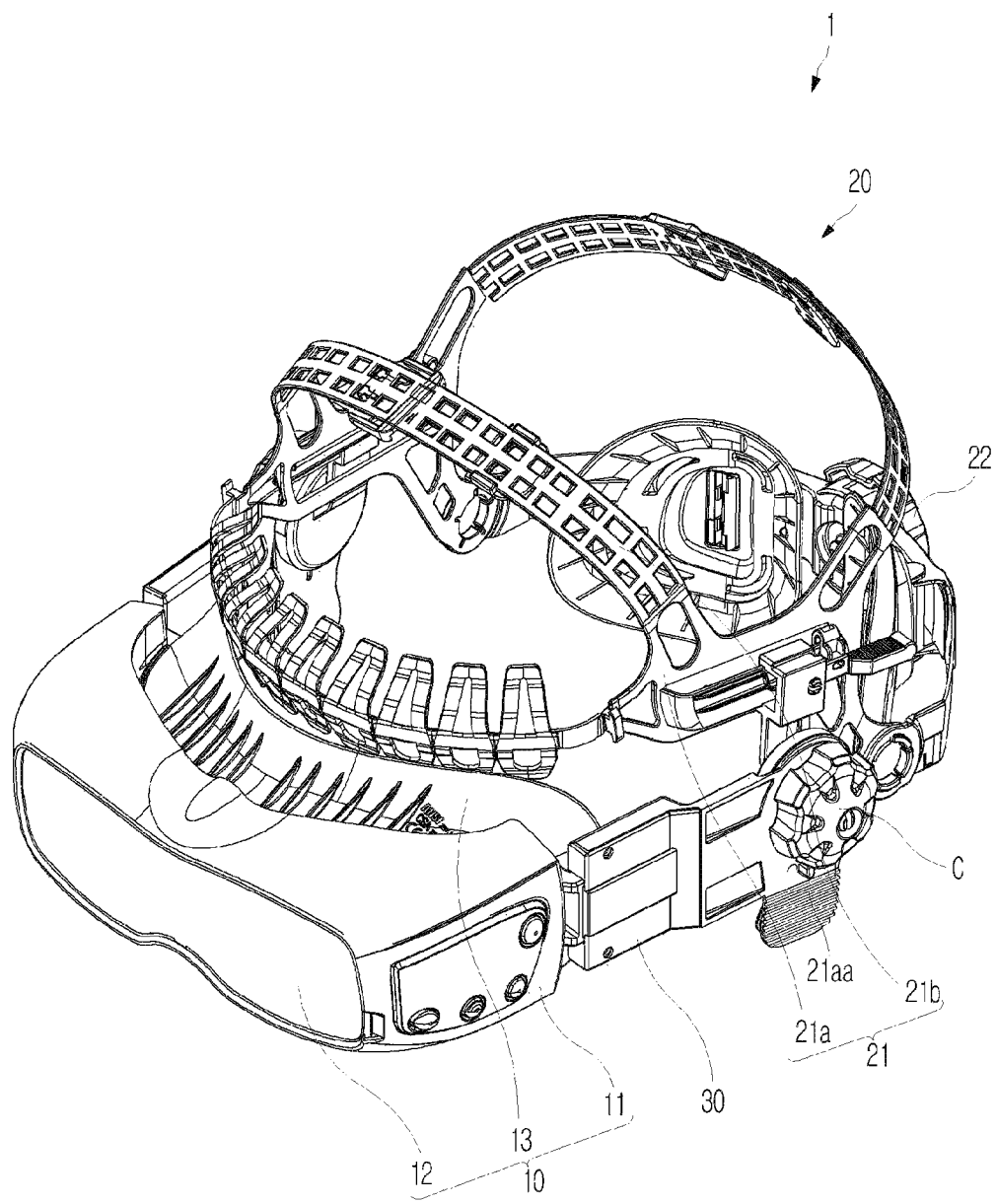
FIG. 2 is a perspective view of facial protection equipment for an easy operation of rotating opening and closing according to one embodiment of the invention.
Figure 3:
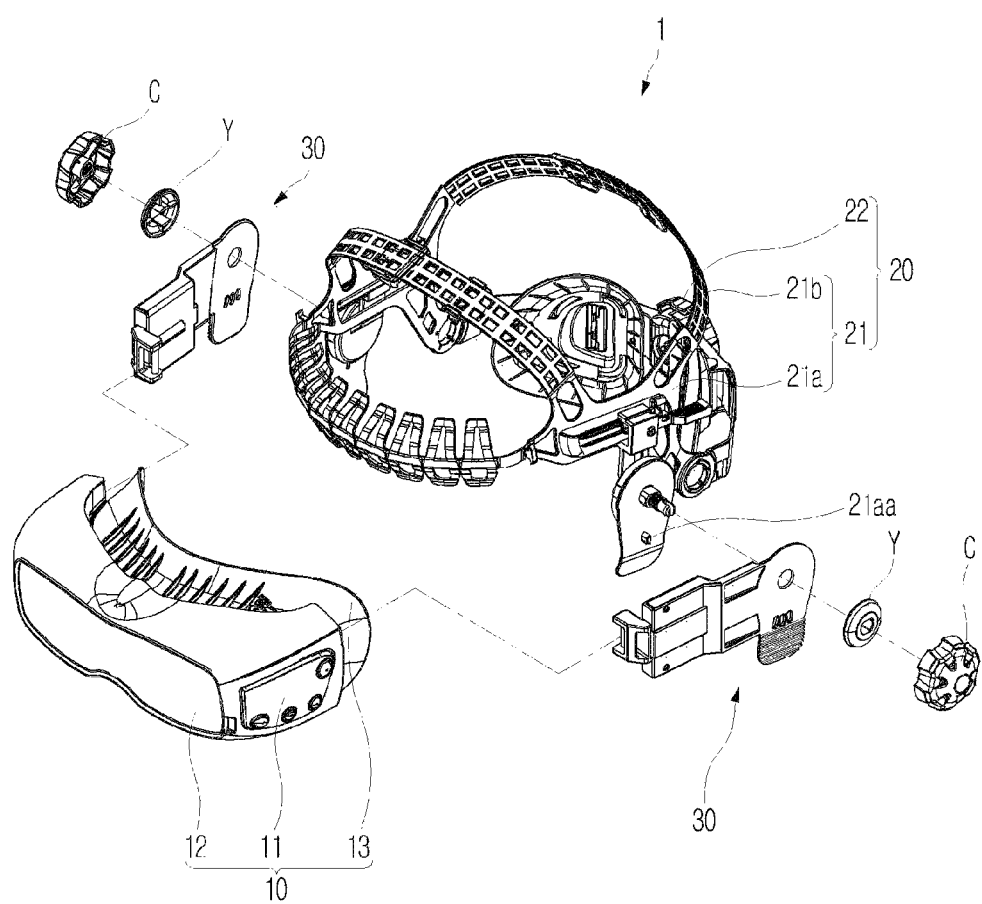
FIG. 3 is an exploded perspective view of the facial protection equipment for an easy operation of rotating opening and closing according to the embodiment of the invention.
Figure 4:
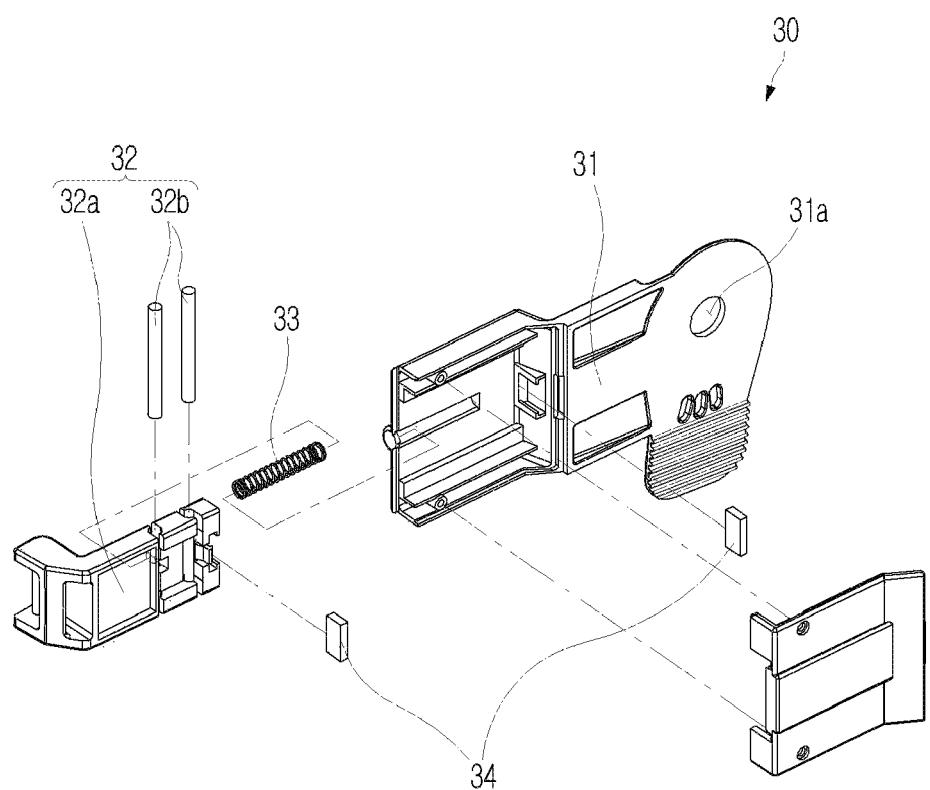
FIG. 4 is an exploded perspective view of a connection member according to the embodiment of the invention.
Figure 5:
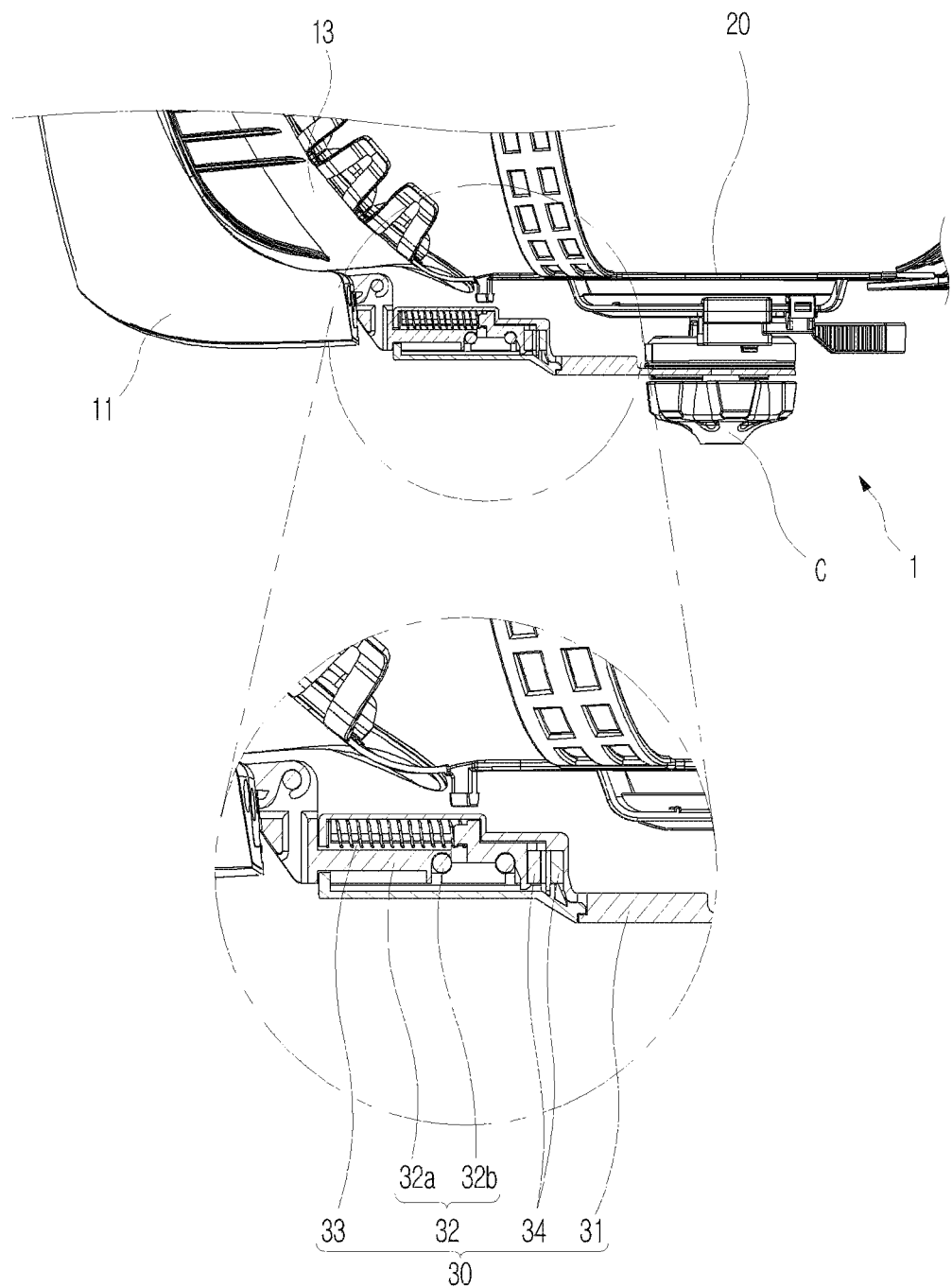
FIG. 5 is a cross-sectional view of the connection member according to the embodiment of the invention.

FIG. 2 is a perspective view of facial protection equipment for an easy operation of rotating opening and closing according to one embodiment of the invention. FIG. 3 is an exploded perspective view of the facial protection equipment for an easy operation of rotating opening and closing according to the embodiment of the invention. FIG. 4 is an exploded perspective view of a connection member according to the embodiment of the invention. FIG. 5 is a cross-sectional view of the connection member according to the embodiment of the invention.

As illustrated in FIGS. 2 to 5, a facial protection equipment (1) for an easy operation of rotating opening and closing according to the embodiment of the invention is configured to include a facial protection unit (10), a fixing unit (20), and a connection member (30).

The facial protection unit (10) is disposed at one side of a face of an operator to shield at least the one side of the face of the operator, thereby, protecting the operator from hazardous light, hazardous fumes, or the like which are produced during a welding operation, and thus a welding mask, a welding goggle, or the like equipped with a light shading lens (12) can be used as the facial protection unit. In the embodiment, the welding goggle is used for convenience of description, and the description thereof is provided.

The facial protection unit (10) includes a main body (11), a light shading lens (12) that is installed at a region of one side of the main body (11), the region corresponding to eyeballs of the operator, and a skirt (13) that is extended from an outer circumference of a rear end portion of the main body (11) toward a rear side and is brought into close contact with the face of the operator around the eyeballs. Here, the skirt (13) fulfills a function of preventing hazardous light, welding spatters, grinder-scattering substances, fume gases, or the like from entering an inside of the main body (11) through a space between the main body (11) and the face of the operator.

The fixing unit (20) is worn on the head of the operator and is connected to the facial protection unit (10) via a connection member (30) to be described below so as to fulfill a function of supporting the facial protection unit such that the facial protection unit (10) is disposed at a position corresponding to the face of the operator.

The fixing unit (20) is configured to have a band portion (21) which is worn around the head of the operator and a length adjusting portion (22) which is coupled to one side of the band portion (21) so as to adjust a length of the band portion (21). Hence, the band portion (21) can be more tightly worn on the head of the operator by tightening the band portion (21) by the length adjusting portion (22) after the band portion (21) is worn on the head of the operator.

Besides, the fixing unit (20) may be configured to include a first band unit (21a) which is worn in a head circumferential direction of the operator so as to be more stably worn on the head of the operator and a second band unit (21b) of which both end portions are coupled to the first band unit (21a) at one side and which is formed to surround an upper portion of the head of the operator.

Besides, the first band unit (21a) has a fixing protrusion (21aa) formed at one side corresponding to a rotation fixing hole (31a) of a pivot bracket (31) to be described below.

Additionally, the first band unit (21a) can be coupled to a cap (C) and a washer (Y) for supporting the connection member (30) such that the connection member coupled to one side of the first band unit does not escape outside.

The connection member (30) is configured to have the pivot bracket (31) of which one end portion is coupled to the one side of the fixing unit (20), a moving bracket (32) of which one end portion is coupled to one side of the pivot bracket (31) to be slidably movable in a length direction of the pivot bracket (31) and the other end portion is connected to the one side of the facial protection unit (10), a returning member (33) which is interposed between the pivot bracket (31) and the moving bracket (32), and magnets (34) which are installed on both the pivot bracket and the moving bracket (32) at one facing side of each other. The connection member fulfills a function of enabling the facial protection unit (10) to easily perform frontward movement when the operator performs rotating opening and closing of the facial protection unit (10).

One end portion of the pivot bracket (31) is coupled to one side of the first band unit (21a) to be rotatable in an up-down direction and has multiple rotation fixing holes (31a) formed at one side of the pivot bracket in a rotating direction. Hence, the one end portion of the pivot bracket is rotated from the first band unit (21a), then, the fixing protrusion (21aa) of the first band unit (21a) is inserted into a rotation fixing hole (31a) at a position corresponding thereto, and thereby a rotation position of the pivot bracket is fixed.

As described above, the pivot bracket (31) is rotated from the first band unit (21a) to supply a rotating force to the facial protection unit (10) and support the moving bracket (32), thereby, fulfilling a function of enabling the fixing unit (20) and the facial protection unit (10) to be tightly connected to each other.

One side of the moving bracket (32) is coupled to the pivot bracket (31) to be slidably movable in a length direction of the pivot bracket (31) in a state of being supported at one side of the pivot bracket (31), and one end portion of the moving bracket is coupled to the one side of the facial protection unit (10).

In this case, the one end portion of the moving bracket (32) may be coupled to the one side of the facial protection unit (10) by a hinge for easy wearing of the facial protection unit (10).

As described above, the above-described moving bracket (32) is coupled to the pivot bracket (31) to be movable in the length direction of the pivot bracket (31), that is, to be movable toward a front side of the facial protection unit (10). Hence, the moving bracket fulfills a function of enabling the facial protection unit (10) to easily move frontward while the moving bracket is moved frontward when the operator performs the rotating opening and closing of the facial protection unit (10).

On the other hand, the moving bracket (32) may be configured to have a moving body (32a) that is slidably coupled to one side of the pivot bracket and a free-rotating member (32b) that is coupled to one side of the moving body (32a) in a freely rotatable manner.

Here, the free-rotating member (32b) is formed into a stick shape having a circular cross section. One side of a center of the free-rotating member is coupled to one side of the moving body (32a) in a freely rotatable manner, both end portions of the free-rotating member are supported at one side of the pivot bracket (31), respectively, such that at least one side of the moving body (32a) is to be disposed separately from the one side of the pivot bracket (31).

When the moving body (32a) slides and moves from the pivot bracket (31), the free-rotating member (32b) fulfills a function of not only enabling the moving body (32a) to be disposed separately from the pivot bracket (31) so as to reduce a frictional force but also enabling the moving body (32a) to easily move as the free-rotating member rotates together with the movement of the moving body (32a) in a state where the free-rotating member is supported at one side of the pivot bracket (31).

The returning member (33) has one end portion which is supported at one side of the pivot bracket (31) and the other end portion is supported at one side of the moving bracket (32) so as to supply an elastic force to the moving bracket (32) in a direction toward the pivot bracket (31), thereby, fulfilling a function of enabling the moving bracket (32) to return to an initial position due to the elastic force when the operator pulls the facial protection unit (10) frontward and finishes an upward rotating opening and closing operation.

As described above, the magnets (34) are installed on the pivot bracket and the moving bracket (32) at one facing side of each other and are formed to have an attractive force to each other. Hence, when the operator pulls the facial protection unit (10) frontward and finishes the upward rotating opening and closing operation, the magnets, together with the returning member (33), fulfill a function of pulling the moving bracket (32) moved due to the attractive force to cause the moving bracket to return to the initial position.

Figure 6:
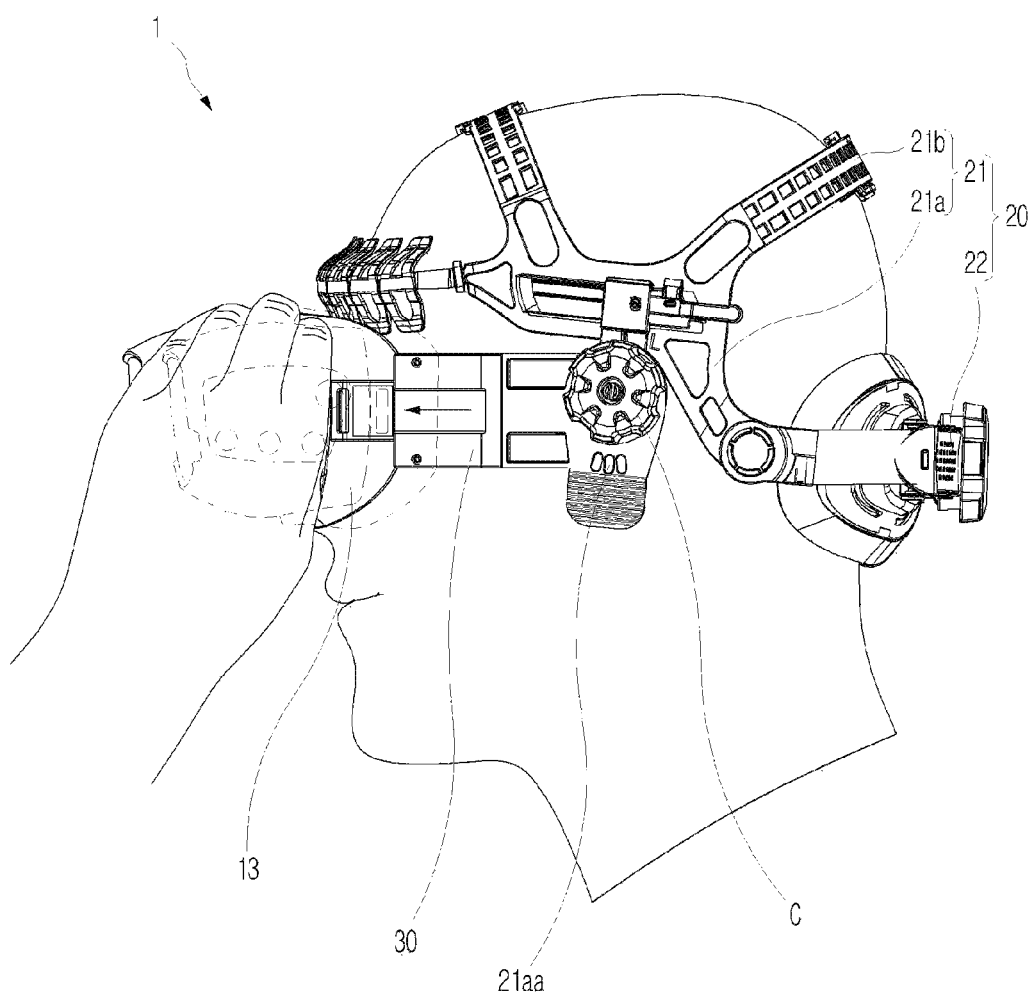
FIG. 6 is a view illustrating a state where the facial protection unit according to the embodiment of the invention is pulled frontward.
Figure 7:
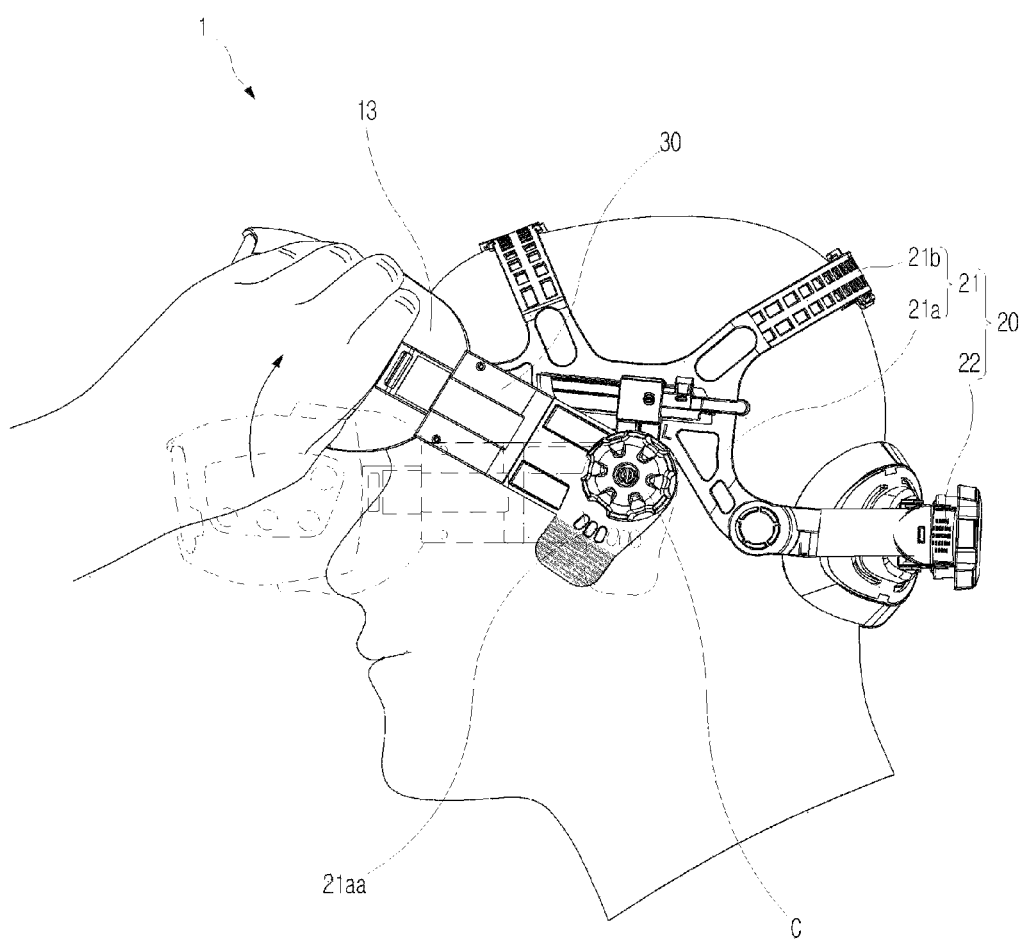
FIG. 7 is a view illustrating a state where the facial protection unit according to the embodiment of the invention is rotated upward.
Figure 8:
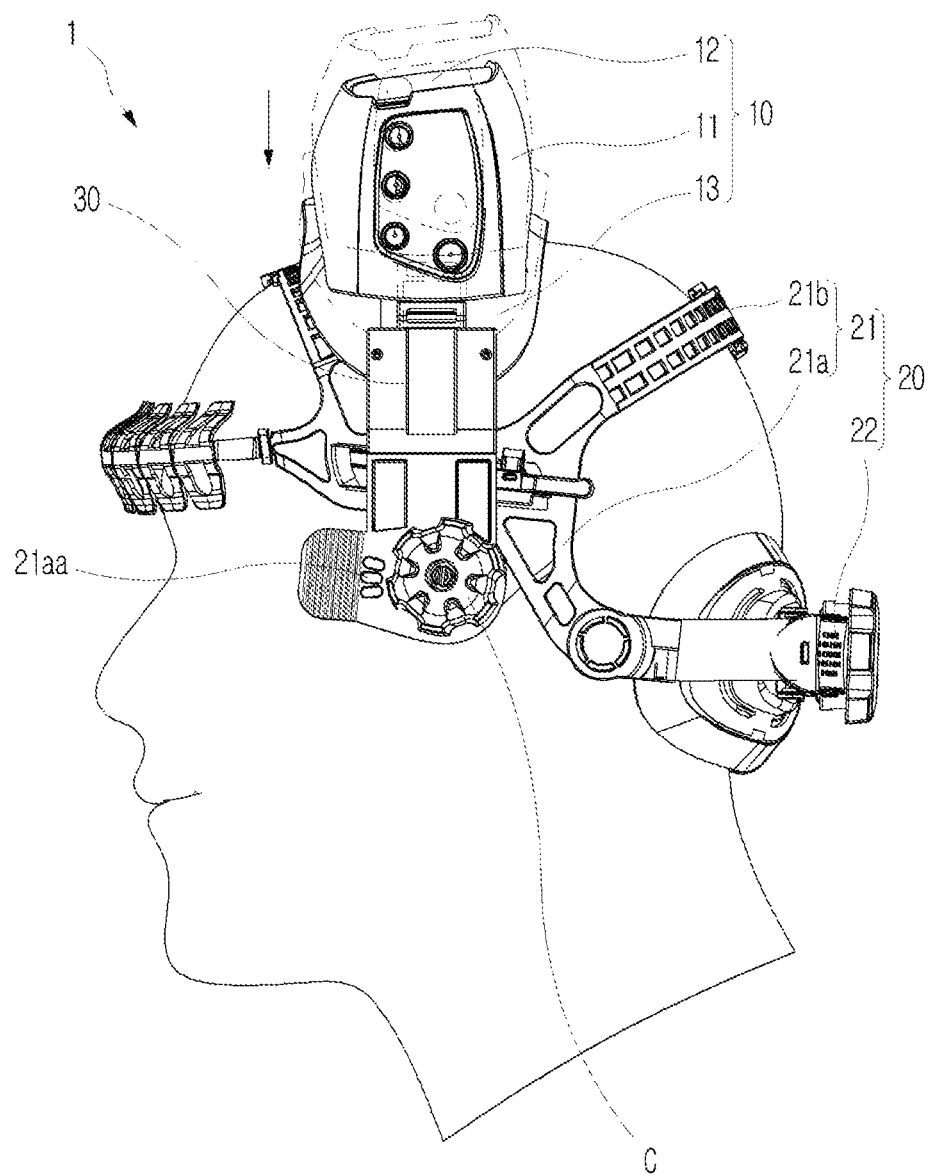
FIG. 8 is a view illustrating a state where the facial protection unit according to the embodiment of the invention is placed on the head.
Figure 9:
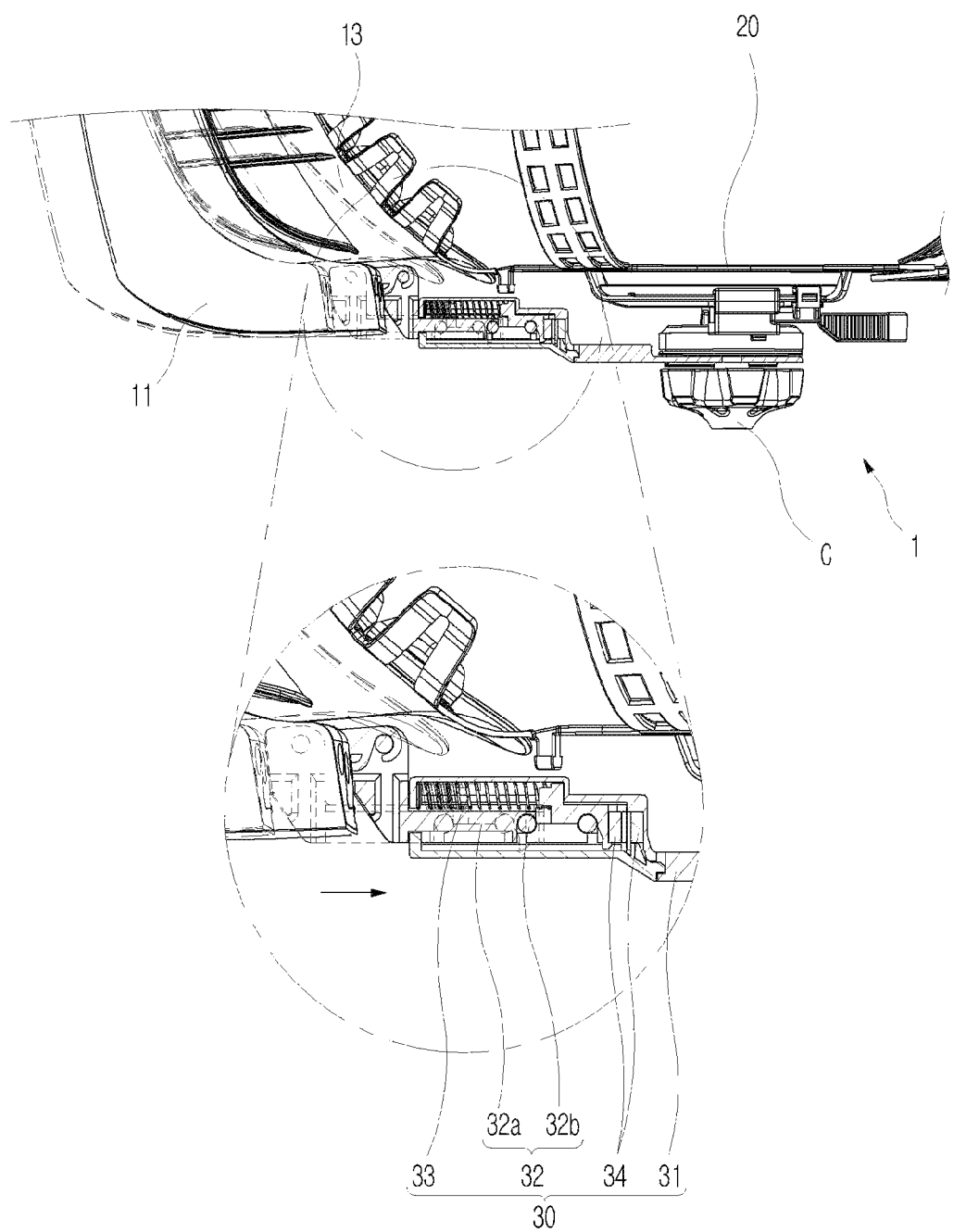
FIG. 9 is a view illustrating a state where the moving bracket according to the embodiment of the invention returns to the initial position.

FIG. 6 is a view illustrating a state where the facial protection unit according to the embodiment of the invention is pulled frontward. FIG. 7 is a view illustrating a state where the facial protection unit according to the embodiment of the invention is rotated upward. FIG. 8 is a view illustrating a state where the facial protection unit according to the embodiment of the invention is placed on the head. FIG. 9 is a view illustrating a state where the moving bracket according to the embodiment of the invention returns to the initial position.

Movement of the facial protection equipment (1) for an easy operation of rotating opening and closing according to the embodiment of the invention, which has such a structure described above, is described as follows, with reference to accompanying FIGS. 6 to 9.

First, the operator performs a welding operation in a state where the skirt (13) of the facial protection unit (10) is brought into close contact with the face of the operator around the eyes.

When the operator wants to place the facial protection unit (10) on the head while the welding operation is performed, the operator pulls the facial protection unit (10) in a state of grabbing one side thereof.

In this case, the free-rotating member (32b) freely rotates while moving frontward in a state where both end portions of the free-rotating member are supported at one side of the pivot bracket (31), and the moving bracket (32) slides and moves frontward from the pivot bracket (31).

As the facial protection unit (10) moves frontward, the skirt (13) is separated from the face of the operator, and the operator releases the facial protection unit (10) after rotating the facial protection unit (10) upward in a state where the skirt (13) is separated from the face.

Therefore, an external force applied to the facial protection unit (10) is removed, and the returning member (33) applies the elastic force to the moving bracket (32) in the direction toward the pivot bracket (31) such that the moving bracket (32) is to be automatically moved to the initial position, and simultaneously the attractive force is generated between the magnet (34) attached to the moving bracket (32) and the magnet (34) attached to the pivot bracket (31). Thus, it is easy for the moving bracket (32) to return to the initial position, and thereby the welding goggle is placed on the head of the operator.

Then, the placement state of the welding goggle can be stably maintained due to the attractive force between the magnet (34) attached to the moving bracket (32) and the magnet (34) attached to the pivot bracket (31).

Additionally, re-wearing movement of the welding goggle is performed in a reverse order of the movement described above, and thus detailed description thereof is omitted.

According to the invention described above, the moving bracket of which the one side is coupled to the facial protection unit is slidably coupled to the one side of the pivot bracket that is rotatably coupled to the one side of the fixing unit, and thereby an effect is achieved in that a front-rear moving operation of the facial protection unit for rotating opening and closing can be easily performed.

Besides, according to the invention, the returning member, which is interposed between the pivot bracket and the connection member, and the magnets, which are installed on both the pivot bracket and the connection member at one facing side of each other, enable returning movement of the moving bracket to be automatically performed after the moving bracket is moved such that another effect is achieved in that rotating opening and closing movement of the facial protection unit can be easily performed.

In addition, according to the invention, the one side of the free-rotating member that is coupled to the one side of the moving bracket in a freely rotatable manner is to be supported at the one side of the inner surface of the pivot bracket such that at least any one side of the moving bracket is separated from the pivot bracket, and thereby still another effect is achieved in that a moving operation of the moving bracket is more easily performed.

While the present invention has been described with respect to the specific embodiments, it will be apparent to those skilled in the art that various changes and modifications may be made without departing from the spirit and scope of the invention as defined in the following claims.

What is claimed is:

1. A facial protection equipment for an easy operation of rotating opening and closing, comprising:
    a facial protection unit of which one side is configured to be supported at one side of a face of an operator and which is configured to shield and protect at least the one side of the face of the operator;
    a fixing unit that is configured to be worn on a head of the operator; and
    a connection member of which one end portion is coupled to one side of the fixing unit to be rotatable in an up-down direction and another end portion is coupled to the facial protection unit,
    wherein the connection member has
    a pivot bracket of which one end portion is coupled to the one side of the fixing unit to be rotatable in the up-down direction and another end portion is extended in one direction, and
    a moving bracket having a predetermined length of which one end portion is coupled to another end portion of the pivot bracket to be slidably movable in a length direction of the pivot bracket and another end portion is connected to the one side of the facial protection unit,
    wherein the connection member further has a returning member that is interposed between the pivot bracket and the moving bracket and supplies an elastic force to the moving bracket in a direction toward the pivot bracket,
    wherein the moving bracket has a moving body that is coupled to the one side of the pivot bracket to be slidably movable in the length direction of the pivot bracket, and a free-rotating member that is coupled to one side of the moving body in a freely rotatable manner and has both end portions which are supported at one side of an inner surface of the pivot bracket.

2. The facial protection equipment for an easy operation of rotating opening and closing according to claim 1,
    wherein the connection member has 1st magnet attached to pivot bracket and 2nd magnet attached to moving bracket to face said 1st magnet.

* * * * *